United States Patent
Beaty et al.

(10) Patent No.: US 6,343,930 B1
(45) Date of Patent: *Feb. 5, 2002

(54) CERAMIC DENTAL ABUTMENTS WITH A METALLIC CORE

(75) Inventors: Keith D. Beaty, Jupiter; Gale R. Brown, Palm City; Richard J. Lazzara, Lake Worth; Stephan S. Porter, Palm Beach Gardens, all of FL (US)

(73) Assignee: Implant Innovations, Inc., Palm Beach Gardens, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/678,811

(22) Filed: Oct. 4, 2000

Related U.S. Application Data

(63) Continuation of application No. 09/304,389, filed on May 4, 1999, now Pat. No. 6,168,435, which is a continuation-in-part of application No. 09/179,493, filed on Oct. 26, 1998, now Pat. No. 5,989,026.

(51) Int. Cl.[7] ............................................... A61C 8/00
(52) U.S. Cl. .................................................... 433/173
(58) Field of Search ................................ 433/172, 173, 433/174, 175, 176, 201.1

(56) References Cited

U.S. PATENT DOCUMENTS

| | | | |
|---|---|---|---|
| 2,721,387 A | 10/1955 | Ashuckian | 32/10 |
| 3,958,471 A | 5/1976 | Müller | 82/1 |
| 4,011,602 A | 3/1977 | Rybicki et al. | 433/173 |
| 4,177,562 A | 12/1979 | Miller et al. | 433/174 |
| 4,259,072 A | 3/1981 | Hirabayashi et al. | 433/173 |
| 4,547,157 A | 10/1985 | Driskell | 433/173 |
| 4,560,353 A | 12/1985 | Schulte et al. | 433/173 |
| 4,575,340 A | 3/1986 | Lustig | 433/173 |
| 4,624,673 A | 11/1986 | Meyer | 623/16 |
| 4,713,004 A | 12/1987 | Linkow et al. | 433/174 |
| 4,738,623 A | 4/1988 | Driskell | 433/173 |

(List continued on next page.)

FOREIGN PATENT DOCUMENTS

| | | | |
|---|---|---|---|
| DE | 21 14 323 | 10/1971 | |
| DE | 21 57 139 | 5/1972 | A61C/13/26 |
| DE | 27 17 506 | 5/1978 | A61F/1/100 |
| DE | 32 24 112 A1 | 2/1984 | A61C/13/30 |

(List continued on next page.)

OTHER PUBLICATIONS

Adell et al., A 15–Year Study Of Osseointegrated In The Treatment Of The Endentulous Jaw, Int. J. Oral Surg., pp. 387–416, 1981.

(List continued on next page.)

*Primary Examiner*—Nicholas D. Lucchesi
(74) *Attorney, Agent, or Firm*—Jenkens & Gilchrist

(57) ABSTRACT

A support post for use with a dental implant comprising a ceramic portion, a screw, and a metal portion. The ceramic portion is adapted to support a prosthesis thereon. The ceramic portion has a supragingival region for protruding beyond the gingiva and a subgingival end for extending into the gingiva. The ceramic portion has a passageway extending therethrough. According to one embodiment, the passageway narrows to form a shoulder that is made entirely of ceramic. The screw is adapted to engage an internally threaded bore in the implant and be insertable through the passageway. The screw comprises a head and a threaded section. The head of the screw seats entirely on the shoulder. The metal portion comprises a lower section and an upper section extending into the passageway. The metal portion abuts the subgingival end of the ceramic portion. The lower section is adapted to receive and engage the corresponding boss of the dental implant. The metal portion has an opening to provide access to the screw.

74 Claims, 8 Drawing Sheets

U.S. PATENT DOCUMENTS

| | | | |
|---|---|---|---|
| 4,746,293 A | 5/1988 | Lundgren et al. | 433/173 |
| 4,758,161 A | 7/1988 | Niznick | 433/173 |
| 4,772,204 A | 9/1988 | Söderberg | 433/174 |
| 4,824,372 A | 4/1989 | Jörnéus et al. | 433/174 |
| 4,846,683 A | 7/1989 | Lazzara et al. | 433/173 |
| 4,850,870 A | 7/1989 | Lazzara et al. | 433/174 |
| 4,850,873 A | 7/1989 | Lazzara et al. | 433/220 |
| 4,854,872 A | 8/1989 | Detsch | 433/173 |
| 4,856,994 A | 8/1989 | Lazzara et al. | 433/173 |
| 4,872,839 A | 10/1989 | Brajnovic | 433/173 |
| 4,904,187 A | 2/1990 | Zingheim | 433/173 |
| 4,955,811 A | 9/1990 | Lazzara | 433/173 |
| 4,978,640 A | 12/1990 | Kelly | 501/32 |
| 4,988,297 A | 1/1991 | Lazzara et al. | 433/173 |
| 4,988,298 A | 1/1991 | Lazzara et al. | 433/173 |
| 5,000,686 A | 3/1991 | Lazzara et al. | 433/174 |
| 5,006,069 A | 4/1991 | Lazzar et al. | 433/173 |
| 5,015,186 A | 5/1991 | Detsch | 433/173 |
| 5,022,860 A | 6/1991 | Lazzara et al. | 433/174 |
| 5,030,096 A | 7/1991 | Hurson et al. | 433/173 |
| 5,035,619 A | 7/1991 | Daftary | 433/173 |
| 5,040,982 A | 8/1991 | Stefan-Dogar | 433/173 |
| 5,040,983 A | 8/1991 | Binon | 433/173 |
| 5,064,373 A | 11/1991 | Stauli et al. | 433/173 |
| 5,071,345 A | 12/1991 | Rosen | 433/17 |
| 5,071,351 A | 12/1991 | Green, Jr. et al. | 433/173 |
| 5,073,111 A | 12/1991 | Daftary | 433/173 |
| 5,082,442 A | 1/1992 | Rosen | 433/17 |
| 5,087,200 A | 2/1992 | Brajnovic et al. | 433/173 |
| 5,100,323 A | 3/1992 | Friedman et al. | 433/173 |
| 5,104,318 A | 4/1992 | Piche et al. | 433/174 |
| 5,105,690 A | 4/1992 | Lazzara et al. | 81/436 |
| 5,106,300 A | 4/1992 | Voitik | 433/173 |
| 5,122,059 A | 6/1992 | Durr et al. | 433/173 |
| 5,125,839 A | 6/1992 | Ingber et al. | 433/169 |
| 5,135,395 A | 8/1992 | Marlin | 433/174 |
| 5,145,371 A | 9/1992 | Jörnéus | 433/173 |
| 5,145,372 A | 9/1992 | Daftary et al. | 433/173 |
| 5,152,687 A | 10/1992 | Amino | 433/173 |
| 5,154,612 A | 10/1992 | Carlsson et al. | 433/173 |
| 5,169,308 A | 12/1992 | Kvist | 433/173 |
| 5,169,309 A | 12/1992 | Staubli et al. | 433/173 |
| 5,188,800 A | 2/1993 | Green, Jr. et al. | 422/23 |
| 5,195,892 A | 3/1993 | Gersberg | 433/173 |
| 5,197,881 A | 3/1993 | Chalifoux | 433/173 |
| 5,209,659 A | 5/1993 | Friedman et al. | 433/173 |
| 5,209,666 A | 5/1993 | Balfour et al. | 433/173 |
| 5,213,502 A | 5/1993 | Daftary | 433/172 |
| 5,246,370 A | 9/1993 | Coatoam | 433/173 |
| 5,281,140 A | 1/1994 | Niznick | 433/172 |
| 5,282,746 A | 2/1994 | Sellers et al. | 433/172 |
| 5,286,195 A | 2/1994 | Clostermann | 433/172 |
| 5,292,252 A | 3/1994 | Nickerson et al. | 433/173 |
| 5,297,963 A | 3/1994 | Daftary | 433/172 |
| 5,316,476 A | 5/1994 | Krauser | 433/173 |
| 5,334,024 A | 8/1994 | Niznick | 433/173 |
| 5,336,090 A | 8/1994 | Wilson, Jr. et al. | 433/172 |
| 5,338,196 A | 8/1994 | Beaty et al. | 433/172 |
| 5,344,457 A | 9/1994 | Pilliar et al. | 623/16 |
| 5,350,300 A | 9/1994 | Gallais | 433/173 |
| 5,362,234 A | 11/1994 | Salazar et al. | 433/173 |
| 5,362,235 A | 11/1994 | Daftary | 433/173 |
| 5,368,483 A | 11/1994 | Sutter et al. | 433/173 |
| 5,417,570 A | 5/1995 | Zuest et al. | 433/173 |
| 5,419,702 A | 5/1995 | Beaty et al. | 433/214 |
| 5,431,567 A | 7/1995 | Daftary | 433/172 |
| 5,433,606 A | 7/1995 | Niznick et al. | 433/173 |
| 5,437,551 A | 8/1995 | Chalifoux | 433/173 |
| 5,447,435 A | 9/1995 | Brodbeck | 433/173 |
| 5,476,382 A | 12/1995 | Daftary | 433/172 |
| 5,476,383 A | 12/1995 | Beaty et al. | 433/214 |
| 5,492,471 A | 2/1996 | Singer | 433/172 |
| 5,533,898 A | 7/1996 | Mena | 433/173 |
| 5,538,426 A | 7/1996 | Harding et al. | 433/172 |
| 5,547,377 A | 8/1996 | Daftary | 433/172 |
| 5,564,924 A | 10/1996 | Kwan | 433/173 |
| 5,571,016 A | 11/1996 | Ingber et al. | 433/173 |
| 5,588,838 A | 12/1996 | Hansson et al. | 433/173 |
| 5,685,714 A | 11/1997 | Beaty et al. | 433/173 |
| 5,829,977 A | 11/1998 | Rogers et al. | 433/172 |

FOREIGN PATENT DOCUMENTS

| | | | | |
|---|---|---|---|---|
| DE | 35 31 389 A1 | 3/1989 | | A61C/8/00 |
| DE | 38 25 601 A1 | 3/1989 | | A61C/8/00 |
| DE | 40 28 855 A1 | 3/1992 | | A61C/8/00 |
| DE | 41 27 839 A1 | 3/1992 | | A61C/8/00 |
| EP | 0 320 024 A1 | 6/1989 | | A61C/8/00 |
| EP | 0 477 644 A1 | 4/1992 | | A61C/8/00 |
| EP | 0 657 146 A1 | 6/1995 | | A61C/8/00 |
| GB | 1 291 470 | 10/1972 | | A61F/1/00 |
| GB | 2 213 065 A | 8/1989 | | A61C/13/30 |
| RU | 1570720 A1 | 6/1990 | | A61C/13/30 |
| WO | WO 85/02337 A1 | 6/1985 | | A61C/8/00 |

OTHER PUBLICATIONS

Core–Vent Corporation, *1989 Core–Vent Implant Symposium*, 3/88.

Dental Imaging Associates, Inc., et al., *The DIA Anatomic Abutment System*, pp. 1–10, 10/91.

DIA™ Dental Dental Imaging Associates, Implamed –The Source, *The Anatomical Abutment System*, pp. 1–1, Oct. 9, 1991.

*EsthetiCon™ systeM Components* (no date).

Lewis, S.G., et al., Single Tooth Implant Supported Restorations, The International Journal of Oral & Maxillofacial Implants, vol. 3, No. 1, pp. 25–30, 1988.

Lewis, S., et al., The "UCLA" Abutment, The International Journal. of Oral & Maxillofacial Implants, vol. 3, No. 3, pp. 183–189, 1988.

New Bio–Esthetic™ Technique Manual, *Abutment Selection And Modification Guide*, Steri–Oss Inc., 1995.

Perri, George, DDS et al., Single Tooth Implants, CDA Journal, vol. 17, No. 3, 3/89.

Zirconium Diboride/Zirconium Carbide/Zirconium Composites for orthopedic applications (no date).

V. A. Ravi, T.D. Claar, B. Berelsman and J. Higgins (no date).

Exhibit A (drawing of healing abutment) (no date).

Exhibit B (assembly drawing of coping and component drawings which comprise coping assembly)(no date).

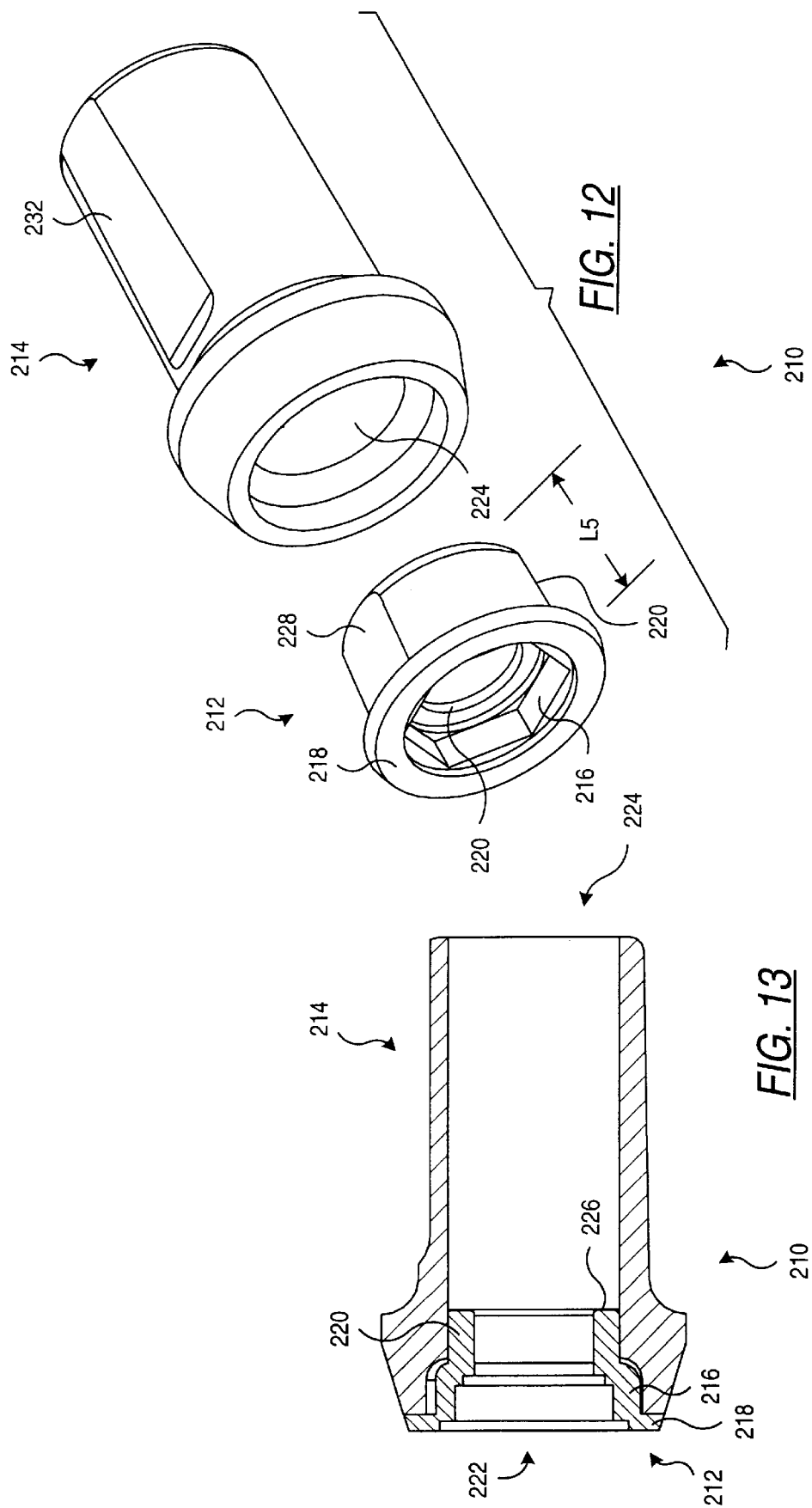

CERAMIC DENTAL ABUTMENTS WITH A METALLIC CORE

CROSS REFERENCE TO RELATED APPLICATIONS

This application is a continuation of U.S. patent application Ser. No. 09/304,389, filed May 4, 1999 now U.S. Pat. No. 6,168,435. U.S. patent application Ser. No. 09/304,389 is a continuation-in-part of U.S. application Ser. No. 09/179,493, filed Oct. 26, 1998 now U.S. Pat. No. 5,989,026.

FIELD OF THE INVENTION

This invention generally relates to a support post for use with a dental implant and adapted to support a prosthesis thereon. Specifically, the support post is comprised of a ceramic portion and a metal portion.

BACKGROUND OF THE INVENTION

Surgical techniques for support of dental prostheses by means of metallic bone-embedded artificial root fixtures are well known. According to one prior art technique, a titanium bone-embedded implant fixture is interfaced with a metallic abutment post on which a superstructure, such as a prosthesis, is supported. The post has an internally shouldered access bore through which a screw is inserted to hold the implant and the post assembled. A number of problems and restrictions are presented, however, in the attachment and retention of the superstructures to such abutment posts.

Specifically, the typical superstructures for use with such posts are made of porcelain. The use of a titanium post generally results in a dark, central rod-like shadow, particularly when exposed to bright light, which makes the prosthesis somewhat unattractive since it is distinguishable from a natural tooth. Further, since the materials are different, sometimes there are problems with securing the prosthesis to the support post.

One attempt to solve the attractiveness and securement problems involves making a support post entirely of ceramic material, specifically, aluminum oxide. This approach allows direct surface bonding by interaction of a porcelain coping and/or prosthesis to the support post, resulting in a secure and almost seamless bond between the prosthesis and support post. While presenting an alternative attraction to the use of a titanium support post, the proposed solution presents a number of problems.

Ceramic materials generally have a much greater hardness than titanium. When a ceramic support post is used, inevitable rocking of the support post due to, for example, chewing, causes a high stress interaction between the metal implant and the ceramic material of the post. Since a ceramic support post is of greater hardness than a titanium implant, it can and does cause damage to the implant. If sufficient damage is caused, eventual surgical intervention is required to remove and replace the titanium implant. In addition, ceramic material is typically not radiopaque. Thus, when examining the juncture between the support post and the titanium implant through conventional dental x-ray imaging, the interface between the two elements is not readily viewable and, thus, adequate x-ray examination cannot be conducted.

SUMMARY OF THE INVENTION

The present invention is a support post for use with a dental implant. The support post comprises a ceramic portion, a screw, and a metal portion. The ceramic portion is adapted to support a prosthesis thereon. The ceramic portion has a supragingival region for protruding beyond the gingiva and a subgingival end for extending into the gingiva. The ceramic portion has a passageway extending therethrough. According to one embodiment of the present invention, the passageway narrows to form a shoulder that is made entirely of ceramic.

The screw is adapted to engage threads of an internally threaded bore in the implant and be insertable through the passageway. The screw comprises a head and a threaded section. The head of the screw seats entirely on the shoulder.

The metal portion comprises a lower section and an upper section extending into the passageway. The metal portion abuts the subgingival end of the ceramic portion. The lower section is adapted to receive and engage a corresponding boss of the dental implant. The metal portion has an opening to provide access to the screw.

BRIEF DESCRIPTION OF THE DRAWINGS

Other objects and advantages of the invention will become apparent upon reading the following detailed description and upon reference to the drawings.

FIG. 12 is an exploded perspective view of a support post including a metal portion and a ceramic portion according to yet another embodiment of the present invention.

FIG. 13 is a side cross-sectional view of a support post of FIG. 12.

Figure 1:
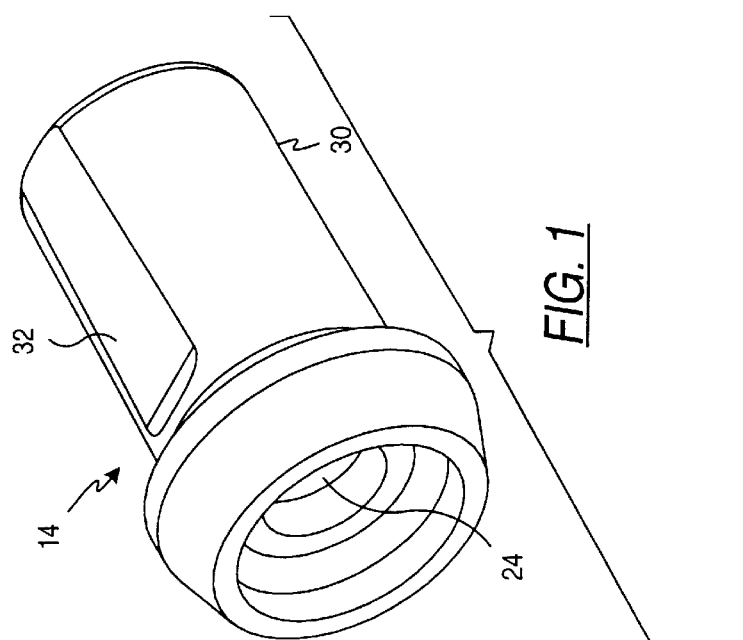
FIG. 1 is an exploded perspective view of a support post including a metal portion and a ceramic portion according to one embodiment of the present invention.

While the invention is susceptible to various modifications and alternative forms, a specific embodiment thereof has been shown by way of example in the drawing and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DESCRIPTION OF ILLUSTRATIVE EMBODIMENTS

Figure 2:
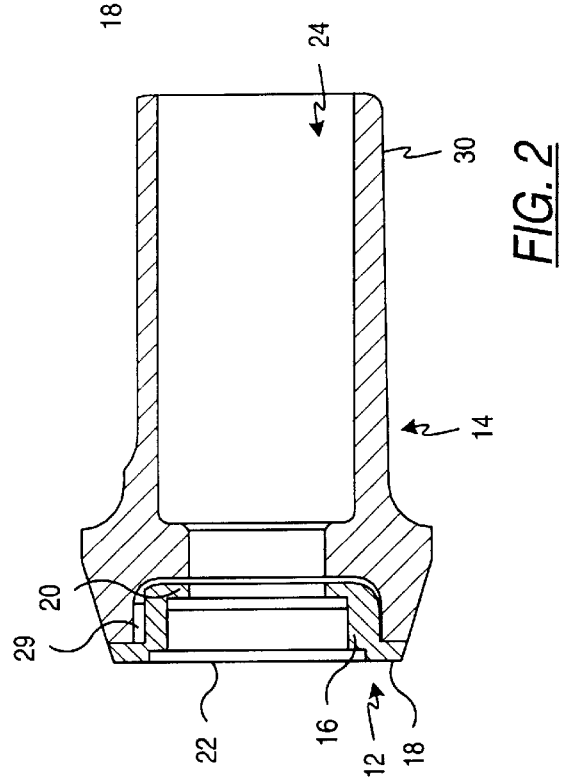
FIG. 2 is a side cross-sectional view of a support post of FIG. 1.
Figure 3:
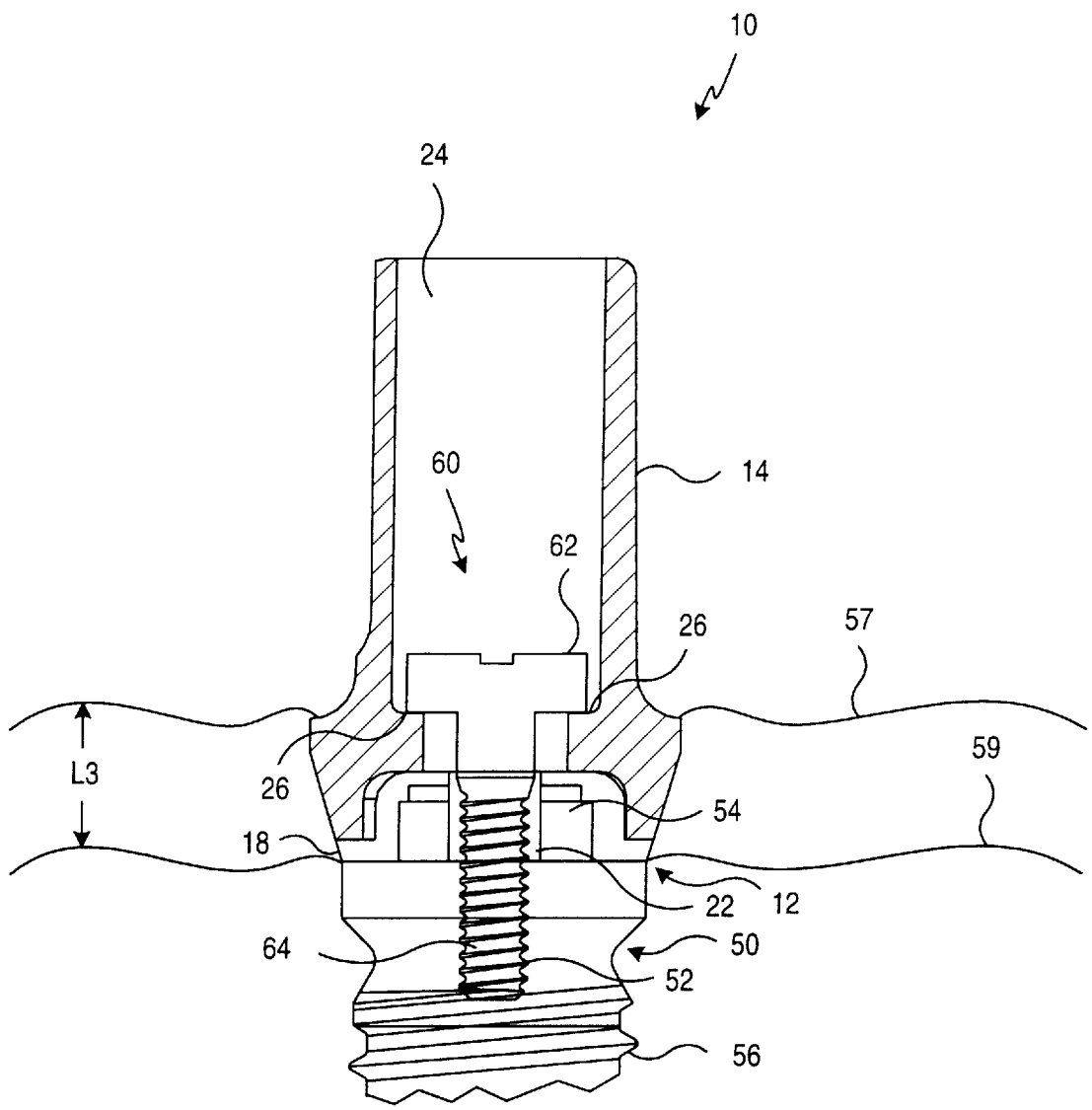
FIG. 3 is a cross-sectional view of a support post of FIG. 2, a dental implant, and an abutment screw according to one embodiment of the present invention.

Referring now to the drawings in detail, FIG. 1 shows an exploded perspective view of a support post 10 that is adapted for use with a dental implant. The support post 10 comprises a metal portion 12 and a ceramic portion 14. FIG. 2 shows a cross-sectional view of the metal portion 12 and the ceramic portion 14 attached together. The metal portion 12 is adapted to receive and engage a dental implant, such as dental implant 50 in FIG. 3. The metal portion 12 of FIGS. 1–3 is shown in more detail in FIGS. 4–6. The ceramic portion 14 is adapted to support a prosthesis thereon (not shown). The ceramic portion 14 of FIGS. 1–3 is shown in more detail in FIGS. 7–9.

Figure 5:
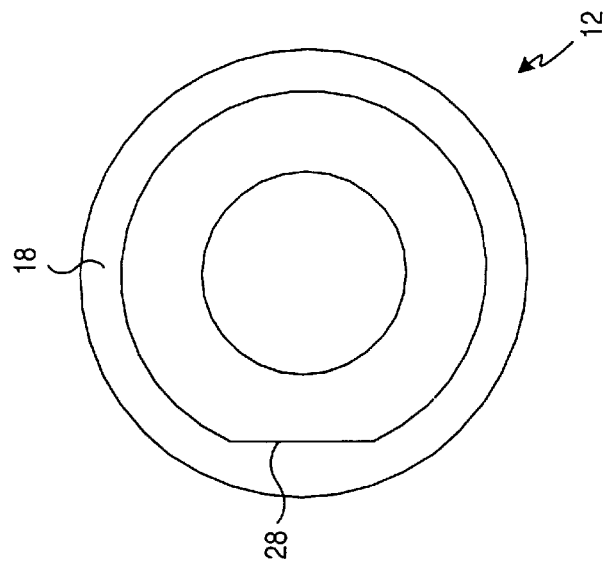
FIG. 5 is a top plan view of the metal portion of FIG. 4.
Figure 4:
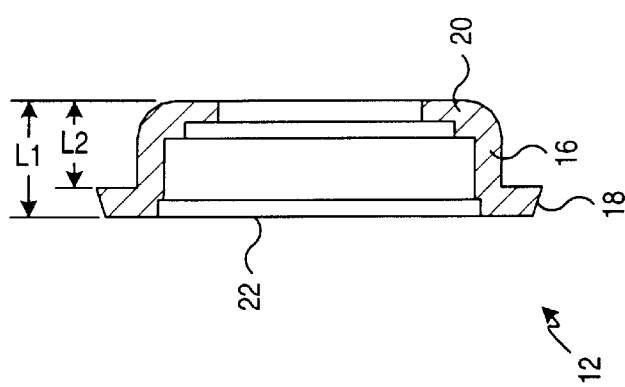
FIG. 4 is a side cross-sectional view of the metal portion of FIG. 1.
Figure 6:
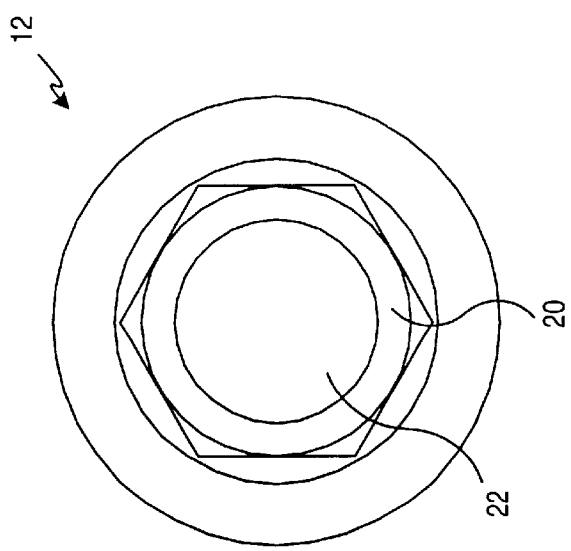
FIG. 6 is a bottom plan view of the metal portion of FIG. 4.

Referring to FIGS. 4–6, the metal portion 12 comprises a lower section and an upper section. The lower section of the metal portion 12 comprises a polygonal socket 16 (e.g., a hexagon) and an outwardly extending flange 18 extending from the polygonal socket 16. The upper section of the metal portion 12 comprises an inwardly extending section 20 extending from the polygonal socket 16. The polygonal socket 16 is adapted to receive and engage a corresponding boss 54 on a gingival end of the dental implant 50 (see, e.g., FIG. 3). The shapes of the polygonal socket 16 and the corresponding polygonal boss 54 inhibit rotation of the support post 10 relative to the dental implant. Referring to FIGS. 3 and 4, the flange 18 has an exterior surface that tapers inwardly toward the dental implant 50. A subgingival end of the ceramic portion 14 has an outer surface that generally follows a contour of the exterior surface of the flange 18.

The metal portion 12 is typically located in a subgingival section (i.e., a section below the gingival surface) so as to enhance the aesthetics of the prosthesis. The length L1 of FIG. 4 is generally from about 1.5 mm to about 3 mm. The length L1 is preferably less that about 3 mm so as to remain below a gingival surface.

The metal portion 12 also includes a generally flat surface 28 (see FIGS. 1 and 5) to assist in inhibiting or preventing rotation of the metal portion 12 relative to the ceramic portion 14. The metal portion 12 is preferably located in a subgingival section (i.e., a section below the gingival surface) so as to enhance the aesthetics of the prosthesis. This is shown, for example, in FIG. 3 where the metal portion 12 is below a gingival surface 57.

To provide access for a screw that engages threads of an internal bore in the dental implant, the metal portion 12 has a central opening 22. As shown in FIGS. 2 and 3, the central opening 22 extends upwardly into a central passageway 24 of the ceramic portion 14. Referring specifically to FIG. 3, a screw 60 is shown extending through the central opening 22. The screw 60 includes a head 62 and a lower section 64 having external threads thereon. The screw 60 is threaded into an internally threaded bore 52 of the dental implant 50. The screw 60 secures the support post 10 and the dental implant 50. The dental implant 50 also has threads 56 for engaging the jawbone (including the maxillary and mandible). The dental implant 50 is substantially located below a gingival surface 57 and contacts a jawbone (not shown). The jawbone is located below a bone tissue surface 59. The length L3 between the gingival surface 57 and the bone tissue surface 59 is generally about 3 mm.

Figure 8:
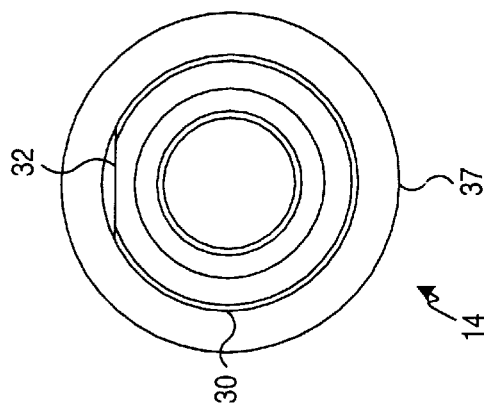
FIG. 8 is a top plan view of the ceramic portion of FIG. 7.
Figure 7:
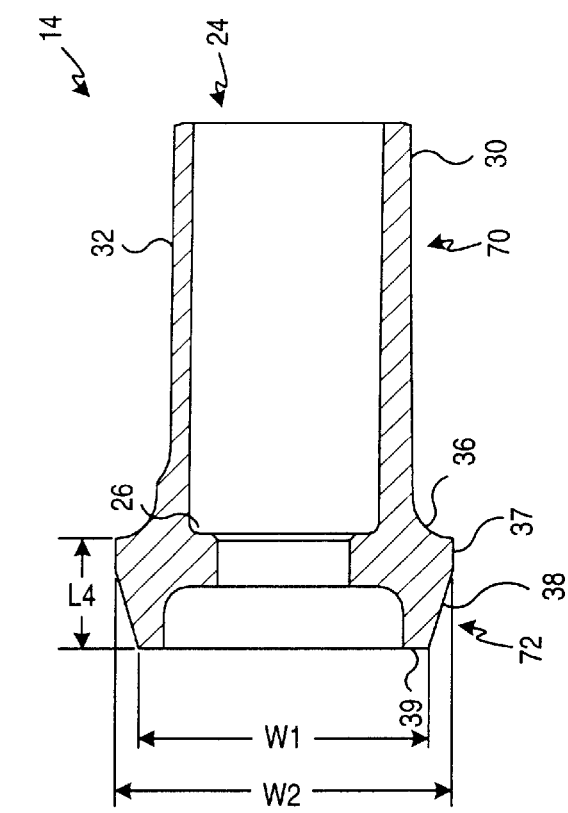
FIG. 7 is a side cross-sectional view of the ceramic portion of FIG. 1.
Figure 9:
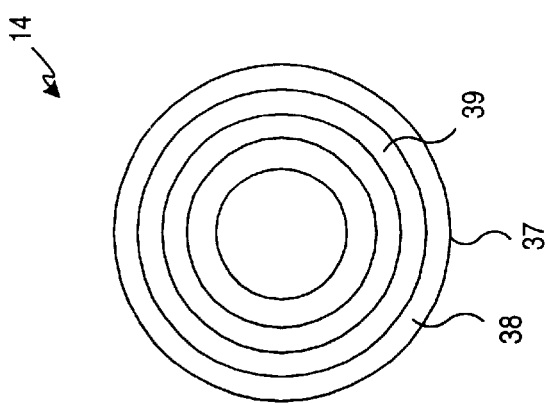
FIG. 9 is a bottom plan view of the ceramic portion of FIG. 7.

Referring to FIGS. 7–9, the ceramic portion 14 includes a supragingival section 70 that protrudes beyond the gingiva, and a subgingival section 72 for extending into the gingiva. The supragingival section 70 includes a generally cylindrical section 30.

The generally cylindrical section 30 of the ceramic portion 14 is adapted to engage a prosthesis (not shown). The generally cylindrical section 30 may be formed into other shapes.

The generally cylindrical section 30 has a generally flat surface portion 32. The surface portion 32 is generally rectangular in shape (see FIG. 1), but may be formed in other shapes, such as, for example, a triangular shape. The surface portion 32 inhibits rotation of a prosthesis (not shown) relative to the support post 10. Specifically, rotation is inhibited or prevented when an adhesive is added to secure a placed prosthesis to the ceramic portion 14. The adhesive is placed in a space formed between an interior surface of a prosthesis and the surface portion 32.

Alternatively, a prosthesis may be formed by building up porcelain. According to one process, the abutment is altered by prepping with a bur to reproduce a shape -and gingival contours of the tooth being replaced. The process begins by building an adaptable type of porcelain on an abutment in rough form and bake. The prosthesis is refined by grinding the contours and the occlusal anatomy to match adjacent teeth on a model. The anatomic shape and contours of the model are verified. The porcelain may be stained to match the color of the adjacent teeth and is typically glazed and polished before delivering.

Additionally, the generally cylindrical section 30 may be tapered slightly to further aid in installing and securing a prosthesis to the support post 10. For example, the generally cylindrical section 30 may be tapered at a pitch of about three degrees. Optionally, the generally cylindrical section 30 may have a groove (not shown) or other means for securing a set screw used to hold a prosthesis in place.

The exterior surface of the generally cylindrical section has a rounded shoulder 36. The rounded shoulder 36 is connected to a generally cylindrical exterior surface 37 that extends generally in a downward direction towards a dental implant. The generally cylindrical exterior surface 37 is connected to a tapered surface 38 that extends inwardly and downwardly towards a dental implant.

Referring specifically to FIG. 7, the ceramic portion 14 is hollow with the central passageway 24 therethrough. At a distal end of the ceramic portion 14, there is an open end which allows a screw to enter into the support post 10. The central passageway 24 narrows to form a shoulder 26 that provides a seat for a screw, such as the head 62 of the screw 60 as shown in FIG. 3. Specifically, the central passageway 24 has a generally horizontal surface defining the shoulder 26. The shoulder 26 of FIG. 7 is made entirely of ceramic.

The length L4 of FIG. 7 may be varied to accommodate differing patient's anatomies. For example, if a patient has a greater gingiva height, the length L4 may be increased. The length L4 is generally from about 2.0 mm to about 4.0 mm. The length L4 may, however, be less than 2.0 mm and greater than 4.0 mm. The length L4 is preferably from about 2 mm to about 3 mm. The length L4 is preferably less than about 3 mm so as to be aesthetically pleasing by remaining below the gingival surface.

The width W1 of FIG. 7 may also vary to accommodate differing patient's anatomies. To provide improved support to the support post, the width W1 is generally selected to correspond to the flange 18 of the metal portion 12. The width W1 is generally from about 3 mm to about 6 mm. The width W1 may, however, be less than 3 mm and greater than 6 mm. A width W2 is generally selected to correspond to the size of the prosthesis and the space between the teeth. The width W2 is typically greater than the width W1. The width W2 is generally from about 5 mm to about 7 mm. The width W2 may, however, be less than 5 mm and greater than 7 mm.

The metal portion 12 is engaged to the ceramic portion 14. Referring back to FIGS. 1 and 2, an exterior surface of the metal portion 12 abuts a corresponding interior surface of the ceramic portion 14 at the subgingival end of the ceramic portion 14. The ceramic portion 14 preferably does not abut a dental implant (see, e.g., FIG. 3).

The metal portion 12 may be engaged to the ceramic portion 14 by a variety of methods. For example, the metal portion 12 may be secured by adhesives to the ceramic portion 14. Some types of adhesives that may be used are conventional cements or ceramic sealants, such as a ceramic sealing glass. The selected adhesive is preferably not affected by temperatures associated with forming a prosthesis by building up porcelain.

The metal portion 12 and the ceramic portion 14 of FIGS. I and 2 may also receive assistance by a screw in their engagement. If a screw seats entirely on a metal portion, then the metal portion and ceramic portion would be held in place, e.g., by only an adhesive.

It is contemplated that other dental adhesives may be used to secure the metal portion 12 to the ceramic portion 14. To form an improved surface for adhesion, the metal portion 12 may be grip-blasted by, for example, air pressure. Alternatively, the metal portion 12 may be made so as to be press-fitted into the ceramic portion 14.

According to one process for securing the metal portion 12 to the ceramic portion 14, ceramic sealing glass is applied to either an exterior surface of the metal portion 12, an interior surface of the ceramic portion 14, or a combination thereof. The metal portion 12 is placed into the interior surface of the ceramic portion 14. The metal portion 12 and the ceramic portion 14 are heated to a temperature sufficient to melt the ceramic sealing glass. The metal portion 12 and the ceramic portion 14 are cooled to a temperature sufficient so as to secure the metal portion 12 to the ceramic portion 14.

Referring to FIGS. 1 and 4, the generally flat surface 28 of the metal portion 12 assists in inhibiting or preventing rotation of the metal portion 12 relative to the ceramic portion 14. Specifically, a space 29 is formed between the ceramic portion 14, and the flat surface 28 of the metal portion 12 receives an adhesive to inhibit or prevent rotation of the metal portion 12 and the ceramic portion 14. If the metal portion 12 and the ceramic portion 14 are press fit, the flat surface 28 of the metal portion 12 does not inhibit or prevent rotation unless a second corresponding generally flat surface (not shown) is formed on an interior surface of the ceramic portion 14.

The metal portion 12 is generally comprised of titanium or a titanium alloy. Other biocompatible materials may be used in forming the metal portion, such as gold alloys, cobalt chrome, and the like. The metal portion 12 may be made of any other medically compatible material having a similar hardness to the hardness of the material used in forming the dental implant. For example, the metal portion 12 may be comprised of Ti—6Al—4V (90 wt % titanium, 6 wt % aluminum, and 4 wt % vanadium) and the dental implant may be comprised of commercially pure titanium or Ti—6Al—4V. The material used to form the metal portion 12 is preferably radiopaque (i.e., opaque to x-rays) so that the interface between the metal portion 12 and a dental implant can be examined.

The ceramic portion 14 may be made entirely of a ceramic material, such as aluminum oxide (alumina). Alternatively, the ceramic portion may be comprised of zirconium oxide (zirconia). The ceramic material may include coloring, such as the natural color of a tooth. To assist in stabilizing the ceramic material, materials, such as hafnium oxide and/or yttrium oxides (yttria), may be added. It is contemplated that additional oxide(s) may be used in forming the ceramic portion 14. In one embodiment, the ceramic portion 14 comprises from about 92 wt % to about 99 wt % zirconium oxide, from about 4.5 wt % to about 5.4 wt % yttrium oxide, from about 0 wt % to about 0.5 wt % hafnium oxide, from about 0 wt % to about 0.5 wt % aluminum trioxide, and from about 0 wt % to about 0.5 wt % of other oxides. The ceramic portion may be made from a material that is radiopaque. The hardness of the material used in forming the ceramic portion is greater than the hardness of the material used in forming the dental implant.

A ceramic portion made from yttria-stabilized zirconium oxide generally has a greater fracture toughness and flexural strength than a ceramic portion of aluminum oxide. It is desirable to have a higher fracture toughness and flexural strength because the ceramic portion is stronger, tougher, and more durable. Also, using a material having a higher fracture toughness and flexural strength may result in faster preparation of the support post if the shaping process can occur at a higher temperature because the material is less likely to chip or crack.

Figure 10:
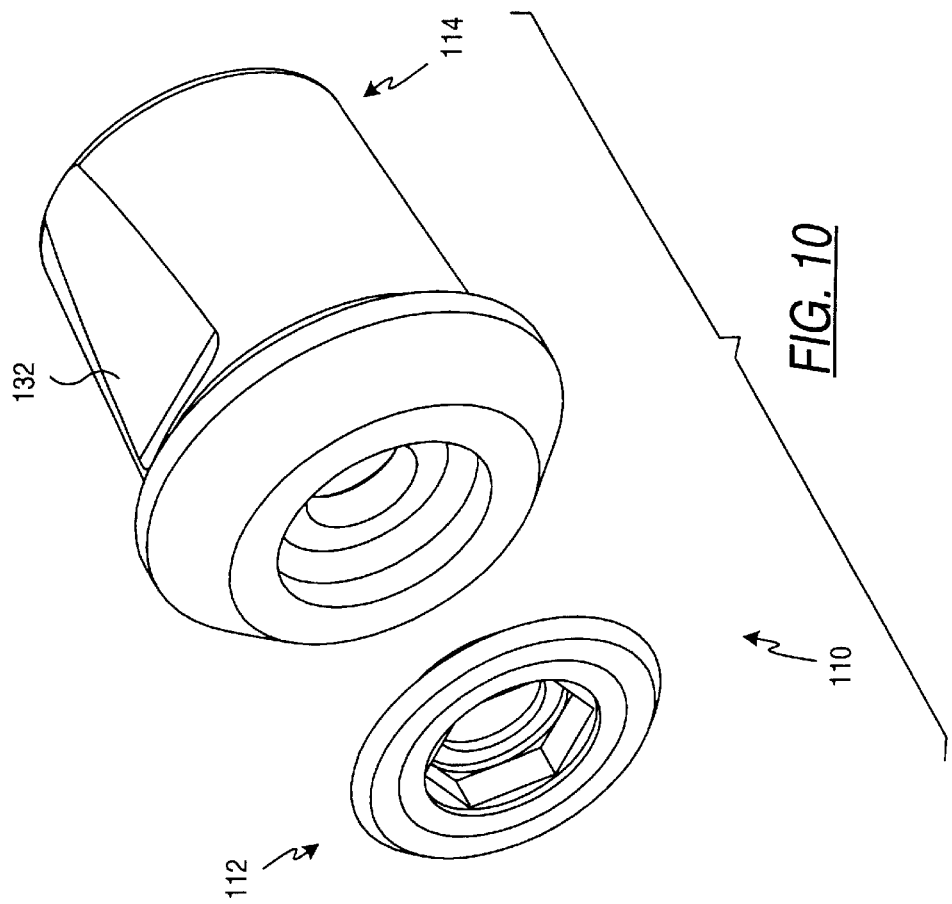
FIG. 10 is an exploded perspective view of a support post including a metal portion and a ceramic portion according to another embodiment of the present invention.
Figure 11:
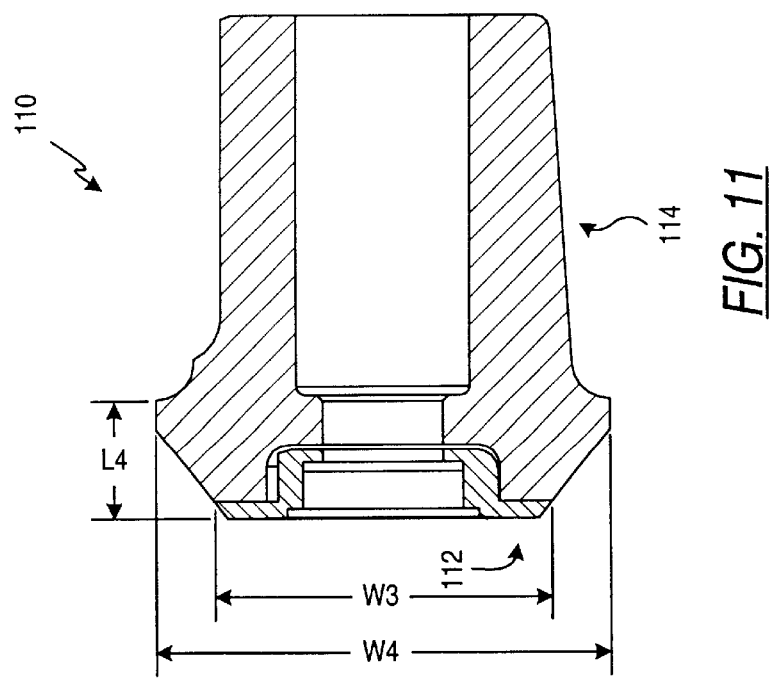
FIG. 11 is a side cross-sectional view of a support post of FIG. 10.

As discussed above, the widths W2 and W1 of the support post 10 may be varied. This is shown, e.g., in FIGS. 10 and 11 where, in another embodiment of a support post (support post 110), the width W3 is greater as compared to the width W1 shown in FIG. 7. Likewise, the width W4 of FIG. 10 is greater than the width W2 shown in FIG. 7. The support post 110 is similar to the support post 10 depicted in FIGS. 1 and 2. The support post 110 includes a metal portion 112 and a ceramic portion 114. The ceramic portion 114 has a surface portion 132 which is a truncated triangle shape.

FIGS. 12–19 illustrate yet another embodiment of a support post (support post 210) to be engaged to an implant and adapted to support a prosthesis thereon. The support post 210 is similar to the support post 10 depicted in FIGS. I and 2, except that a generally tubular section 220 has a greater length L5 than a corresponding length L2 of the metal portion 12 (see FIG. 4). The support post 210 of FIGS. 12 and 13 includes a metal portion 212 and a ceramic portion 214.

Figure 15:
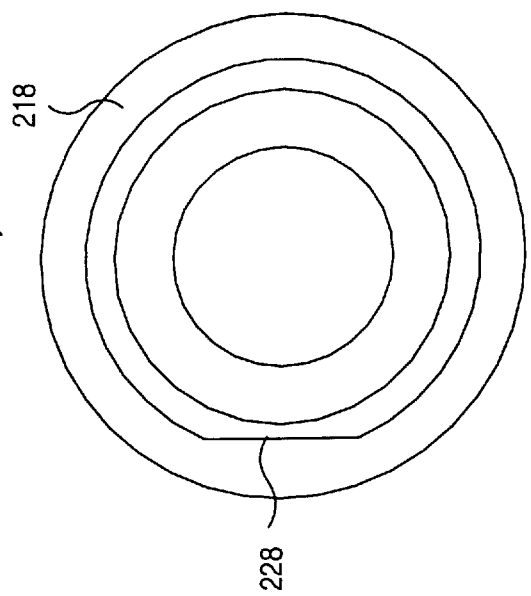
FIG. 15 is a top plan view of the metal portion of FIG. 14.
Figure 14:
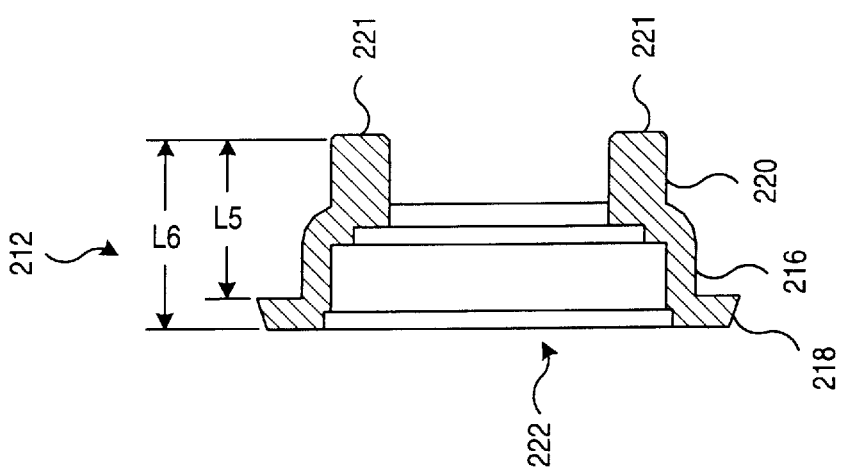
FIG. 14 is a side cross-sectional view of the metal portion of FIG. 12.
Figure 16:
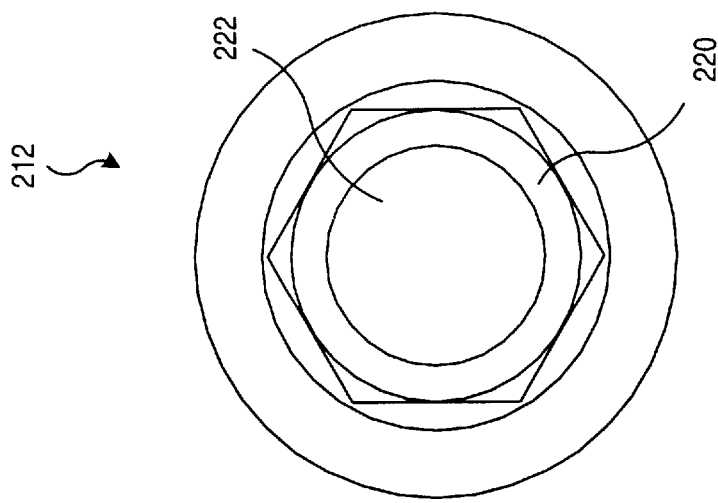
FIG. 16 is a bottom plan view of the metal portion of FIG. 14.

Referring to FIGS. 14–16, the metal portion 212 comprises a polygonal socket 216, an outwardly extending flange 218 extending from the polygonal socket 216, and the generally tubular section 220 extending above the polygonal socket 216. The generally tubular section 220 has an upper surface 221. At least a portion of the upper surface 221 forms a shoulder that provides a seat for a head of a screw (not shown). The portion of the upper surface 221 forming the shoulder is made entirely of metal. To provide access for a screw to reach internal threads in the dental implant, the metal portion 212 has a central opening 222. The metal portion 212 may be located in a subgingival section (ie., a section below the gingival surface) so as to enhance the aesthetics of the prosthesis. The length L6 is generally from about 1.5 mm to about 4 mm and, more specifically, from about 2 mm to about 3 mm. The length L6 is preferably less that about 3 mm so as to remain below a gingival surface.

Figure 18:
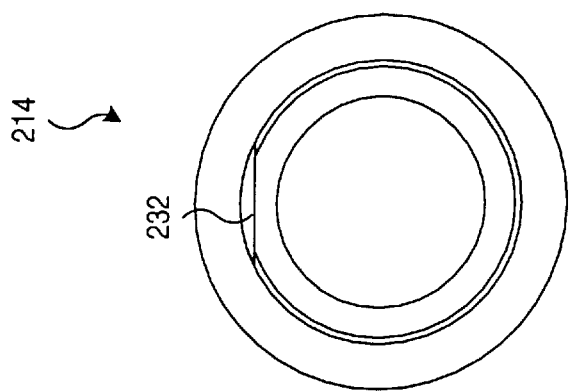
FIG. 18 is a top plan view of the ceramic portion of FIG. 17.
Figure 17:
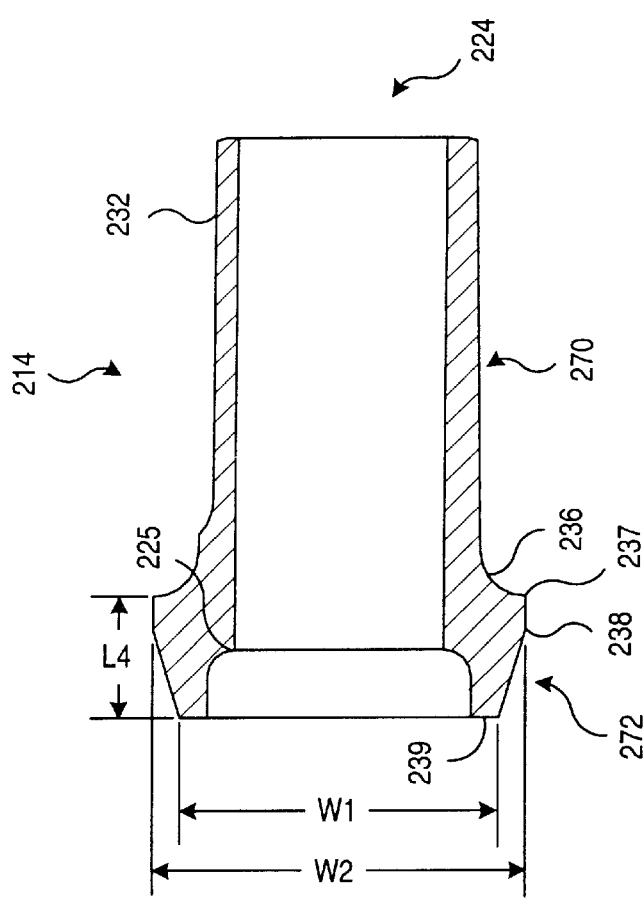
FIG. 17 is a side cross-sectional view of the ceramic portion of FIG. 12.
Figure 19:
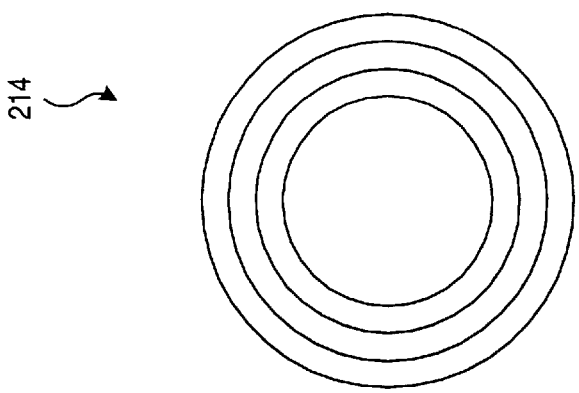
FIG. 19 is a bottom plan view of the ceramic portion of FIG. 17.

Another embodiment of the ceramic portion is shown in FIGS. 17–19. The ceramic portion 214 differs from the ceramic portion 14 by, e.g., not forming a shoulder to seat the screw. The ceramic portion 214 of FIGS. 17–19 is adapted to engage the metal portion 212.

The ceramic portion 214 of FIGS. 17–19 includes a supragingival section 270 (i.e., a section above the gingival surface) and a subgingival section 272 (i.e., a section below the gingival surface). The ceramic portion 214 is hollow with a central passageway 224 therethrough. The central passageway 224 widens at an internally rounded shoulder 225 in a generally horizontal direction before proceeding in a generally vertical direction.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. A support post for use with a dental implant, said dental implant having an internally threaded bore and a non-round fitting located at a gingival end portion thereof, said implant being substantially located below an exterior surface of the gingiva and contacting a jawbone, said support post comprising:
   a ceramic portion adapted to support a prosthesis thereon, said ceramic portion having a supragingival region for protruding beyond said gingiva and a subgingival end below said supragingival region, said ceramic portion having a passageway extending therethrough, said passageway narrowing to form a shoulder, said shoulder being made entirely of ceramic;
   a screw adapted to engage threads of said internally threaded bore in said implant and insertable through said passageway, said screw comprising a head and a threaded section, said head of said screw seats entirely on said shoulder; and
   a metal portion extending into said passageway and engaging said subgingival end of said ceramic portion, said metal portion having a lower section for engaging said corresponding non-round fitting of said dental implant and an opening to provide access to said screw.

2. The support post of claim 1, wherein said ceramic portion is comprised of aluminum oxide, zirconium oxide, or a combination thereof.

3. The support post of claim 2, wherein said ceramic portion is comprised of zirconium oxide.

4. The support post of claim 3, wherein said ceramic portion further includes hafnium oxide, yttrium oxide, or a combination thereof.

5. The support post of claim 2, wherein said ceramic portion further includes hafnium oxide, yttrium oxide, or a combination thereof.

6. The support post of claim 1, wherein said metal portion is comprised of titanium, a titanium alloy, a gold alloy or cobalt chrome.

7. The support post of claim 1, wherein said passageway includes a generally horizontal surface defining said shoulder.

8. The support post of claim 1, wherein said lower section of said metal portion comprises a flange.

9. The support post of claim 8, wherein said flange has an exterior surface, said exterior surface tapering inwardly toward said dental implant.

10. The support post of claim 9, wherein said subgingival end of said ceramic portion has an outer surface generally following a contour of said exterior surface of said flange.

11. The support post of claim 1, wherein said upper section of said metal portion is generally tubular.

12. A support post for use with a dental implant, said dental implant having an internally threaded bore, said implant being substantially located below an exterior surface of the gingiva and contacting a jawbone, comprising:
   a supragingival section comprised of a ceramic material and having a passageway extending therethrough, said supragingival section adapted to support a prosthesis thereon, said passageway narrowing to form a shoulder, said shoulder being made entirely of ceramic;
   a screw adapted to engage threads of said internally threaded bore in said implant and insertable through said passageway, said screw comprising a head and a threaded section, said head of said screw seats entirely on said shoulder; and
   a subgingival section including means for contacting said dental implant, at least a portion of said subgingival section being made of metal, said subgingival section having an opening to provide access to said screw.

13. The support post of claim 12, further including a ceramic sealant.

14. The support post of claim 13, wherein said ceramic sealant is a ceramic sealant glass.

15. The support post of claim 13, wherein said metal portion has a flat surface, and wherein a space formed between said flat surface and an inner surface of said passageway of said ceramic portion receives a majority of said ceramic sealant.

16. The support post of claim 12, further comprising an implant.

17. The support post of claim 12, wherein said ceramic is aluminum oxide, zirconium oxide, or a combination thereof.

18. The support post of claim 17, wherein said ceramic is zirconium oxide.

19. The support post of claim 18, wherein said ceramic further includes hafnium oxide, yttrium oxide, or a combination thereof.

20. The support post of claim 17, wherein said ceramic further includes hafnium oxide, yttrium oxide, or a combination thereof.

21. The support post of claim 12, wherein said metal is comprised of titanium, a titanium alloy, a gold alloy or cobalt chrome.

22. The support post of claim 12, wherein said passageway includes a generally horizontal surface defining said shoulder.

23. The support post of claim 12, wherein said contacting means comprises a flange.

24. The support post of claim 23, wherein said flange has an exterior surface, said exterior surface tapering inwardly toward said dental implant.

25. The support post of claim 12, wherein a portion of said subgingival section is made from ceramic.

26. The support post of claim 1, wherein said non-round fitting is a boss.

27. The support post of claim 1, further including a ceramic sealant.

28. The support post of claim 27, wherein said ceramic sealant is a ceramic sealant glass.

29. The support post of claim 27, wherein said metal portion has a flat surface, and wherein a space formed between said flat surface and an inner surface of said passageway of said ceramic portion receives a majority of said ceramic sealant.

30. The support post of claim 1, further comprising an implant.

31. A support post for use with a dental implant, said dental implant having an internally threaded bore and a non-round fitting located at a gingival end portion thereof, said implant being substantially located below an exterior surface of the gingiva and contacting a jawbone, said support post comprising:
   a ceramic portion adapted to support a prosthesis thereon, said ceramic portion having a supragingival region for protruding beyond said gingiva and a subgingival end below said supragingival region, said ceramic portion having a passageway extending therethrough;
   a metal portion comprising a lower section, an upper section extending into said passageway, and an opening, said metal portion engaging said subgingival end of said ceramic portion, said lower section adapted to receive and engage said corresponding non-round fitting of said dental implant, said upper section having an uppermost surface forming a shoulder; and
   a screw adapted to engage said internal threads in said implant, said screw passing through said opening, said screw seating entirely on said uppermost surface of said upper section of said metal portion.

32. The support post of claim 31, wherein said ceramic portion is comprised of aluminum oxide, zirconium oxide, or a combination thereof.

33. The support post of claim 32, wherein said ceramic portion is comprised of zirconium oxide.

34. The support post of claim 33, wherein said ceramic portion further includes hafnium oxide, yttrium oxide, or a combination thereof.

35. The support post of claim 32, wherein said ceramic portion further includes hafnium oxide, yttrium oxide, or a combination thereof.

36. The support post of claim 31, wherein said metal portion is comprised of titanium, a titanium alloy, gold alloy or a cobalt chrome.

37. The support post of claim 31, wherein said passageway includes a generally horizontal surface defining said shoulder.

38. The support post of claim 31, wherein said lower section of said metal portion comprises a flange.

39. The support post of claim 38, wherein said flange has an exterior surface, said exterior surface tapering inwardly toward said dental implant.

40. The support post of claim 39, wherein said subgingival end of said ceramic portion has an outer surface generally following a contour of said exterior surface of said flange.

41. The support post of claim 31, wherein said upper section of said metal portion is generally tubular.

42. The support post of claim 31, wherein said non-round fitting is a boss.

43. The support post of claim 31, further including a ceramic sealant.

44. The support post of claim 43, wherein said ceramic sealant is a ceramic sealant glass.

45. The support post of claim 43, wherein said metal portion has a flat surface, and wherein a space formed between said flat surface and an inner surface of said passageway of said ceramic portion receives a majority of said ceramic sealant.

46. The support post of claim 31, further comprising an implant.

47. A prosthesis support post for use with a dental implant positioned below an exterior surface of the gingiva and contacting bone, said dental implant including an internally threaded bore and a gingival end portion with a non-round fitting, said support post comprising:
   a metal portion for engaging said gingival end portion of said implant and including a flange;
   a ceramic portion having a subgingival end for extending below said exterior surface of said gingiva and a supragingival region for protruding beyond said gingiva, said subgingival end engaging said flange, said ceramic portion further including an internal surface defining a passageway, said internal surface defining a shoulder; and
   a screw extending through said passageway and for holding said support post on said implant via engagement with said internally threaded bore, said screw seating entirely on said shoulder of said passageway.

48. The support post of claim 42, wherein said ceramic portion is comprised of aluminum oxide, zirconium oxide, or a combination thereof.

49. The support post of claim 48, wherein said ceramic portion further includes hafnium oxide, yttrium oxide, or a combination thereof.

50. The support post of claim 42, wherein said metal portion is comprised of titanium, a titanium alloy, a gold alloy or cobalt chrome.

51. The support post of claim 42, wherein said passageway includes a generally horizontal surface defining said shoulder.

52. The support post of claim 42, wherein said flange has an exterior surface, said exterior surface tapering inwardly toward said dental implant and wherein said subgingival end of said ceramic portion has an outer surface generally following a contour of said exterior surface of said flange.

53. The support post of claim 42, wherein an upper section of said metal portion is generally tubular.

54. The support post of claim 42, wherein said non-round fitting is a boss.

55. The support post of claim 42, further including a ceramic sealant.

56. The support post of claim 55, wherein said ceramic sealant is a ceramic sealant glass.

57. The support post of claim 55, wherein said metal portion has a flat surface, and wherein a space formed between said flat surface and an inner surface of said passageway of said ceramic portion receives a majority of said ceramic sealant.

58. The support post of claim 42, further comprising an implant.

59. A prosthesis support post for use with a dental implant positioned below an exterior surface of the gingiva and contacting bone, said implant having a gingival end portion with a non-round fitting, said support post comprising:
   a metal portion for engaging said gingival end portion of said implant and including a flange;
   a generally tubular ceramic portion having a lower internal cavity into which at least a part of said metal portion is received, said ceramic portion including a subgingival end engaging said flange and a supragingival region for protruding beyond said gingiva, said ceramic portion having an internal shoulder residing above said lower internal cavity; and
   a screw for extending through said ceramic portion and for said support post on said implant, said screw seating on said shoulder.

60. The support post of claim 59, wherein said ceramic portion is comprised of aluminum oxide, zirconium oxide, or a combination thereof, and wherein said metal portion is comprised of titanium, a titanium alloy, a gold alloy or cobalt chrome.

61. The support post of claim 59, wherein said internal shoulder is a generally horizontal surface.

62. The support post of claim 59, wherein said non-round fitting is a boss.

63. The support post of claim 59, further including a ceramic sealant.

64. The support post of claim 63, wherein said ceramic sealant is a ceramic sealant glass.

65. The support post of claim 63, wherein said metal portion has a flat surface, and wherein a space formed between said flat surface and an inner surface of said passageway of said ceramic portion receives a majority of said ceramic sealant.

66. The support post of claim 59, further comprising an implant.

67. A support post for use with a dental implant, said dental implant having an internally threaded bore, said support post comprising:

a ceramic portion having an upper portion, a lower portion and a passageway extending therethrough, said passageway narrowing to form a shoulder;

a metal insert residing in said passageway of said lower portion of said ceramic portion and being entirely below said shoulder; and a screw adapted to engage said internal threads in said implant and insertable through said passageway, said screw comprising a head and a threaded section, said head of screw seats entirely on said shoulder.

68. The support post of claim 67, wherein said metal insert forms a non-round fitting adapted to engage a corresponding fitting of said dental implant.

69. The support post of claim 67, further including a ceramic sealant.

70. The support post of claim 69, wherein said ceramic sealant is a ceramic sealant glass.

71. The support post of claim 69, wherein said metal insert has a flat surface, and wherein a space formed between said flat surface and an inner surface of said passageway of said ceramic portion receives a majority of said ceramic sealant.

72. The support post of claim 67, further comprising an implant.

73. A combination of a dental implant and a support post for use with said dental implant, the combination comprising:

said dental implant having an internally threaded bore and a non-round fitting located at a gingival end portion thereof, said implant being substantially located below an exterior surface of the gingiva and contacting a jawbone; and said support post comprising a ceramic portion, a screw and a metal portion, said ceramic portion adapted to support a prosthesis thereon, said ceramic portion having a supragingival region for protruding beyond said gingiva and a subgingival end below said supragingival region, said ceramic portion having a passageway extending therethrough, said passageway narrowing to form a shoulder, said shoulder being made entirely of ceramic, said screw adapted to engage threads of said internally threaded bore in said implant and insertable through said passageway, said screw comprising a head and a threaded section, said head of said screw seats entirely on said shoulder, and said metal portion extending into said passageway and engaging said subgingival end of said ceramic portion, said metal portion having a lower section for engaging said corresponding non-round fitting of said dental implant and an opening to provide access to said screw.

74. A combination of a dental implant and a support post for use with said dental implant, the combination comprising:

said dental implant having an internally threaded bore, said implant being substantially located below an exterior surface of the gingiva and contacting a jawbone; and said support post comprising a supragingival section, a screw and a subgingival section, said supragingival section comprised of a ceramic material and having a passageway extending therethrough, said supragingival section adapted to support a prosthesis thereon, said passageway narrowing to form a shoulder, said shoulder being made entirely of ceramic, said screw adapted to engage threads of said internally threaded bore in said implant and insertable through said passageway, said screw comprising a head and a threaded section, said head of said screw seats entirely on said shoulder, and said subgingival section including means for contacting said dental implant, at least a portion of said subgingival section being made of metal, said subgingival section having an opening to provide access to said screw.

* * * * *